United States Patent
Lashinski

(10) Patent No.: US 8,753,370 B2
(45) Date of Patent: Jun. 17, 2014

(54) DUAL ENDOVASCULAR FILTER AND METHODS OF USE

(75) Inventor: Randall T. Lashinski, Windsor, CA (US)

(73) Assignee: Claret Medical, Inc., Santa Rosa, CA (US)

(*) Notice: Subject to any disclaimer, the term of this patent is extended or adjusted under 35 U.S.C. 154(b) by 56 days.

(21) Appl. No.: 12/844,420

(22) Filed: Jul. 27, 2010

(65) Prior Publication Data

US 2011/0022076 A1    Jan. 27, 2011

Related U.S. Application Data

(60) Provisional application No. 61/228,703, filed on Jul. 27, 2009.

(51) Int. Cl.
*A61M 29/00* (2006.01)

(52) U.S. Cl.
USPC ............ 606/200; 606/113; 606/128; 606/159

(58) Field of Classification Search
USPC ............................ 606/113–200; 604/48, 229; 623/1.1–1.15
See application file for complete search history.

(56) References Cited

U.S. PATENT DOCUMENTS

| | | |
|---|---|---|
| 3,472,230 A | 10/1969 | Fogarty |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,873,978 A | 10/1989 | Ginsburg |
| 5,108,419 A | 4/1992 | Reger |

(Continued)

FOREIGN PATENT DOCUMENTS

| | | |
|---|---|---|
| DE | 10049812 | 4/2002 |
| EP | 1400257 A2 | 3/2004 |

(Continued)

OTHER PUBLICATIONS

Lee et al.; U.S. Appl. No. 12/871,708 entitled "Intravascular Blood Filters and Methods of Use," filed Aug. 30, 2010.

(Continued)

*Primary Examiner* — Katherine Dowe
*Assistant Examiner* — Sidharth Kapoor
(74) *Attorney, Agent, or Firm* — Knobbe Martens Olson & Bear LLP

(57) ABSTRACT

Blood filter devices and methods of use is describe herein. Present invention pertains to a method of filtering and capturing particles in a vasculature of a patient that comprises steps of introducing a delivery device, which has a filter assembly placed therein, through a first vessel. The filter assembly comprises a first filter portion and second filter portion that open and closes with respect to each other via a pivot axis extending perpendicular to a longitudinal axis of delivery catheter. Upon deployment of the filter assembly the first filter portion is positioned relative to the first vessel such that particles traveling into the first vessel will be trapped in the first filter portion, and positioning the second filter portion relative to the second vessel such that particles traveling into the second vessel will be trapped in the second filter portion. After capturing the particles in the respective filters, first and second filter portions pivot towards one another to close the filter assembly in order to be retrieved back into the delivery device for removal from the vasculature of the patient.

9 Claims, 8 Drawing Sheets

(56) References Cited

U.S. PATENT DOCUMENTS

| | | | |
|---|---|---|---|
| 5,192,286 | A | 3/1993 | Phan |
| 5,613,980 | A * | 3/1997 | Chauhan .................. 606/194 |
| 5,662,671 | A | 9/1997 | Barbut et al. |
| 5,707,389 | A | 1/1998 | Louw et al. |
| 5,766,151 | A | 6/1998 | Valley et al. |
| 5,779,716 | A | 7/1998 | Cano et al. |
| 5,814,064 | A | 9/1998 | Daniel |
| 5,827,324 | A | 10/1998 | Cassell |
| 5,833,650 | A | 11/1998 | Imran |
| 5,848,964 | A | 12/1998 | Samuels |
| 5,910,154 | A * | 6/1999 | Tsugita et al. ............ 606/200 |
| 5,911,734 | A | 6/1999 | Tsugita et al. |
| 5,935,139 | A | 8/1999 | Bates |
| 5,980,555 | A | 11/1999 | Barbut et al. |
| 5,993,469 | A | 11/1999 | McKenzie et al. |
| 6,001,118 | A | 12/1999 | Daniel |
| 6,010,522 | A * | 1/2000 | Barbut et al. ............. 606/200 |
| 6,027,520 | A | 2/2000 | Tsugita et al. |
| 6,042,598 | A | 3/2000 | Tsugita et al. |
| 6,083,239 | A | 7/2000 | Addis |
| 6,096,053 | A | 8/2000 | Bates |
| 6,099,534 | A * | 8/2000 | Bates et al. .............. 606/127 |
| 6,120,494 | A | 9/2000 | Jonkman |
| 6,142,987 | A | 11/2000 | Tsugita |
| 6,152,946 | A | 11/2000 | Broome et al. |
| 6,171,328 | B1 | 1/2001 | Addis |
| 6,179,851 | B1 | 1/2001 | Barbut et al. |
| 6,235,045 | B1 | 5/2001 | Barbut et al. |
| 6,245,087 | B1 | 6/2001 | Addis |
| 6,245,088 | B1 | 6/2001 | Lowery |
| 6,245,089 | B1 | 6/2001 | Daniel |
| 6,264,663 | B1 | 7/2001 | Cano |
| 6,270,513 | B1 | 8/2001 | Tsugita et al. |
| 6,309,399 | B1 | 10/2001 | Barbut et al. |
| 6,325,815 | B1 | 12/2001 | Kusleika et al. |
| 6,336,934 | B1 | 1/2002 | Gilson et al. |
| 6,346,116 | B1 | 2/2002 | Brooks et al. |
| 6,361,545 | B1 | 3/2002 | Macoviak et al. |
| 6,364,900 | B1 | 4/2002 | Heuser |
| 6,371,971 | B1 | 4/2002 | Tsugita et al. |
| 6,383,174 | B1 | 5/2002 | Eder |
| 6,383,205 | B1 | 5/2002 | Samson et al. |
| 6,485,502 | B2 | 11/2002 | Don Michael et al. |
| 6,517,559 | B1 | 2/2003 | O'Connell |
| 6,558,356 | B2 | 5/2003 | Barbut |
| 6,605,102 | B1 | 8/2003 | Mazzocchi et al. |
| 6,620,148 | B1 | 9/2003 | Tsugita |
| 6,663,652 | B2 | 12/2003 | Daniel et al. |
| 6,712,835 | B2 | 3/2004 | Mazzocchi |
| 6,726,651 | B1 | 4/2004 | Robinson et al. |
| 6,726,701 | B2 | 4/2004 | Gilson et al. |
| 6,740,061 | B1 | 5/2004 | Oslund |
| 6,830,579 | B2 | 12/2004 | Barbut |
| 6,843,798 | B2 | 1/2005 | Kusleika et al. |
| 6,872,216 | B2 | 3/2005 | Daniel |
| 6,887,258 | B2 | 5/2005 | Denison et al. |
| 6,905,490 | B2 | 6/2005 | Parodi |
| 7,011,094 | B2 | 3/2006 | Rapacki et al. |
| 7,048,752 | B2 | 5/2006 | Mazzocchi |
| 7,094,249 | B1 | 8/2006 | Broome et al. |
| 7,115,134 | B2 | 10/2006 | Chambers |
| 7,160,255 | B2 | 1/2007 | Saadat |
| 7,169,165 | B2 | 1/2007 | Belef et al. |
| 7,214,237 | B2 | 5/2007 | Don Michael et al. |
| 7,323,001 | B2 | 1/2008 | Clubb et al. |
| 7,410,491 | B2 | 8/2008 | Hopkins |
| 7,493,154 | B2 | 2/2009 | Bonner et al. |
| 7,559,925 | B2 | 7/2009 | Goldfarb et al. |
| 7,572,272 | B2 | 8/2009 | Denison et al. |
| 7,766,961 | B2 | 8/2010 | Patel et al. |
| 7,922,732 | B2 | 4/2011 | Mazzocchi et al. |
| 7,998,104 | B2 | 8/2011 | Chang |
| 8,372,108 | B2 | 2/2013 | Lashinski |
| 8,382,788 | B2 | 2/2013 | Galdonik |
| 8,518,073 | B2 | 8/2013 | Lashinski |

| Publication Number | | Date | Inventor |
|---|---|---|---|
| 2001/0041858 | A1 | 11/2001 | Ray et al. |
| 2002/0026145 | A1 | 2/2002 | Bagaoisan et al. |
| 2002/0055767 | A1 | 5/2002 | Forde et al. |
| 2002/0077596 | A1 | 6/2002 | McKenzie et al. |
| 2002/0095172 | A1 | 7/2002 | Mazzocchi et al. |
| 2002/0123761 | A1 | 9/2002 | Barbut et al. |
| 2003/0100919 | A1 | 5/2003 | Hopkins et al. |
| 2003/0171770 | A1 | 9/2003 | Kusleika et al. |
| 2004/0002730 | A1 * | 1/2004 | Denison et al. ............. 606/200 |
| 2004/0064092 | A1 | 4/2004 | Tsugita et al. |
| 2004/0093015 | A1 | 5/2004 | Ogle |
| 2004/0193206 | A1 | 9/2004 | Gerberding |
| 2004/0215167 | A1 | 10/2004 | Belson |
| 2004/0220611 | A1 | 11/2004 | Ogle |
| 2004/0225321 | A1 | 11/2004 | Krolik et al. |
| 2004/0230220 | A1 | 11/2004 | Osborne |
| 2004/0243175 | A1 | 12/2004 | Don Michael |
| 2004/0254601 | A1 | 12/2004 | Eskuri |
| 2004/0254602 | A1 | 12/2004 | Lehe et al. |
| 2005/0010285 | A1 | 1/2005 | Lambrecht et al. |
| 2005/0080356 | A1 | 4/2005 | Dapolito et al. |
| 2005/0101987 | A1 | 5/2005 | Salahieh |
| 2005/0137696 | A1 | 6/2005 | Salahieh |
| 2005/0177132 | A1 | 8/2005 | Lentz et al. |
| 2006/0015136 | A1 | 1/2006 | Besselink |
| 2006/0015138 | A1 | 1/2006 | Gertner |
| 2006/0030877 | A1 | 2/2006 | Martinez et al. |
| 2006/0089666 | A1 | 4/2006 | Linder et al. |
| 2006/0100658 | A1 | 5/2006 | Obana et al. |
| 2006/0100662 | A1 | 5/2006 | Daniel et al. |
| 2006/0129180 | A1 | 6/2006 | Tsugita et al. |
| 2006/0149350 | A1 | 7/2006 | Patel et al. |
| 2006/0161241 | A1 | 7/2006 | Barbut et al. |
| 2006/0200191 | A1 | 9/2006 | Zadno-Azizi |
| 2006/0259066 | A1 | 11/2006 | Euteneuer |
| 2007/0088383 | A1 | 4/2007 | Pal et al. |
| 2007/0191880 | A1 | 8/2007 | Cartier et al. |
| 2007/0244504 | A1 | 10/2007 | Keegan et al. |
| 2008/0004687 | A1 | 1/2008 | Barbut et al. |
| 2008/0058860 | A1 * | 3/2008 | Demond et al. ............. 606/200 |
| 2008/0065145 | A1 | 3/2008 | Carpenter |
| 2008/0065147 | A1 | 3/2008 | Mazzocchi et al. |
| 2008/0125848 | A1 | 5/2008 | Kusleika et al. |
| 2008/0188884 | A1 | 8/2008 | Gilson et al. |
| 2008/0234722 | A1 | 9/2008 | Bonnette et al. |
| 2008/0262442 | A1 | 10/2008 | Carlin et al. |
| 2009/0024072 | A1 | 1/2009 | Criado et al. |
| 2009/0024153 | A1 | 1/2009 | Don Michael |
| 2009/0069840 | A1 | 3/2009 | Hallisey |
| 2009/0198269 | A1 | 8/2009 | Hannes et al. |
| 2009/0203962 | A1 | 8/2009 | Miller et al. |
| 2009/0254172 | A1 * | 10/2009 | Grewe .................. 623/1.15 |
| 2009/0326525 | A1 | 12/2009 | Galdonik et al. |
| 2010/0004633 | A1 | 1/2010 | Rothe et al. |
| 2010/0063537 | A1 | 3/2010 | Ren et al. |
| 2010/0179583 | A1 | 7/2010 | Carpenter et al. |
| 2010/0179584 | A1 | 7/2010 | Carpenter et al. |
| 2010/0179585 | A1 | 7/2010 | Carpenter et al. |
| 2010/0179647 | A1 | 7/2010 | Carpenter et al. |
| 2010/0185216 | A1 | 7/2010 | Garrison et al. |
| 2010/0185231 | A1 | 7/2010 | Lashinski |
| 2010/0191276 | A1 | 7/2010 | Lashinski |
| 2010/0211095 | A1 | 8/2010 | Carpenter |
| 2010/0312268 | A1 | 12/2010 | Belson |
| 2010/0324589 | A1 | 12/2010 | Carpenter et al. |
| 2011/0022076 | A1 | 1/2011 | Lashinski |
| 2011/0066221 | A1 | 3/2011 | White et al. |
| 2011/0282379 | A1 | 11/2011 | Lee et al. |
| 2012/0046739 | A1 | 2/2012 | Von Oepen et al. |
| 2012/0203265 | A1 | 8/2012 | Heuser |
| 2013/0231694 | A1 | 9/2013 | Lashinski |

FOREIGN PATENT DOCUMENTS

| | | |
|---|---|---|
| EP | 1253871 | 2/2007 |
| JP | 2011-525405 A | 9/2011 |
| WO | WO 99/23976 | 5/1999 |
| WO | WO 2004/026175 | 4/2004 |
| WO | WO 2008/100790 A2 | 8/2008 |

(56) References Cited

FOREIGN PATENT DOCUMENTS

| WO | WO 2008/113857 | | 9/2008 |
|---|---|---|---|
| WO | WO 2010/008451 | | 1/2010 |
| WO | WO 2010/083527 | A2 | 7/2010 |
| WO | WO 2010/088520 | A2 | 8/2010 |
| WO | WO 2011/034718 | A2 | 3/2011 |
| WO | WO 2011/017103 | A2 | 10/2011 |
| WO | PCT/US2011/067598 | | 12/2011 |

OTHER PUBLICATIONS

International Search Report in Application No. PCT/US2010/021417 dated Aug. 23, 2010, in 4 pages.
International Search Report in Application No. PCT/US2010/047166 dated Apr. 27, 2011, in 7 pages.
International Search Report in Application No. PCT/US2010/043390 dated Apr. 8, 2011, in 11 pages.
International Search Report in Application No. PCT/US2011/067598 dated May 10, 2012, in 45 pages.
International Preliminary of Patentability in Application No. PCT/US2010/022590 dated Jan. 29, 2010, in 4 pages.
Office Action for U.S. Appl. No. 13/383,488 dated Sep. 5, 2013, in 18 pages.

\* cited by examiner

DUAL ENDOVASCULAR FILTER AND METHODS OF USE

CROSS-REFERENCE TO RELATED APPLICATIONS

This application claims the benefit of U.S. Provisional Application No. 61/228,703, filed Jul. 27, 2009, entitled "Dual Endovascular Filter and Methods of Use", which application is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. A common problem in endovascular catheterization is that plaque found in the diseased vessels and valves can be dislodged and result in embolization. A major drawback to endovascular treatment of cardiac valves and arteries in the heart or thoracic aorta is that the dislodged debris can embolize into the carotid vessels resulting in catastrophic consequences such as stroke or even death. Attempts have been made to protect the cerebral vasculature with filters and other devices, but the inadequacy of the present art is obvious in the fact that these devices are rarely used. The pending patent applications for such protection devices suggests both the inadequacy of the present art and the need for improved devices not to deflect the emboli but to capture and remove the emboli from the body.

The majority of devices described are filters. The problems with filters include difficulty in placement and retrieval as well as the possibility that a filter will fill abruptly causing blockage of the artery prior to removal of the filter. Cerebral protection requires placement of filters in the carotid arteries, which has the additional drawback of manipulation of the carotid vessels during filter placement while the cerebral vasculature is still unprotected. The risk of stroke for a carotid arteriogram done by cannulation of the carotid artery is 1% compared to an arteriogram done from injection into the aorta without selective cannulation which carries minimal risk. The risk of cannulating a carotid artery, navigating a catheter containing a filter into position, and deploying the filter would likely carry an even higher stroke risk. Patients requiring cardiac or aortic arch procedures are high risk candidates for having carotid disease. The chance of causing a stroke by the placement of the protective device into both carotid arteries makes the risk of using these devices prohibitive. The time and skill necessary to selectively cannulate both carotid arteries for filter placement has also contributed to the decision not to use them despite the stroke risk of unprotected cardiac and aortic arch procedures.

BRIEF DESCRIPTION OF THE INVENTION

The present invention comprises an embolic filter device. In use, the invention is placed into the aortic arch by the access via right-radial or brachial entry, preferably through the right arm but it may also be placed via the femoral artery or other access point used by interventional procedures such as the carotid artery. In one embodiment, the device is deployed partially in the aortic arch but also in the innominate artery and carotid artery. Additionally or alternatively, the device may deploy to protect the left subclavian artery, where the device is opened and pulled back into position to cover the ostia of both the brachiocephalic and left common carotid arteries. A portion of the device, typically extending from a common hinged frame protrudes into the vessel(s) with a portion of the device entering into the vessel or artery to trap emboli. In some embodiments the portion of the device arising from the common frame has a cone, funnel or other shape adapted or configured for positioning within the vessel lumen to filter emboli.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
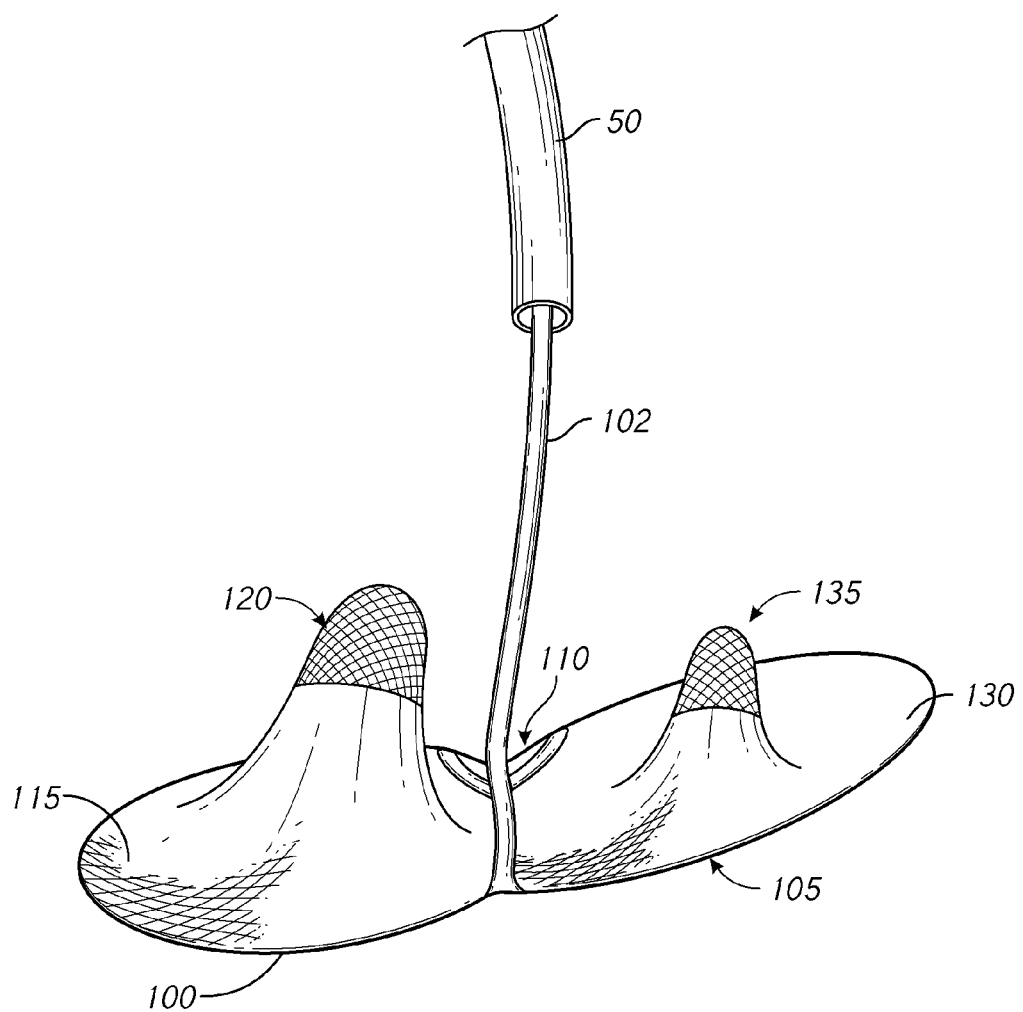
FIG. 1 depicts a schematic version of the filter device extending from the delivery catheter.

In one embodiment, filter device 100 of the present invention is positioned prior to any manipulation of the heart or thoracic aorta. FIG. 1 illustrates the filter device 100. The filter device 100 includes a frame 105 having a hinge or collapsible joint 110 connected to shaft 102. The frame 105 has a generally circular shape that contains two filter portions 115, 130. The filter portions 115, 130 extend out of plane with the frame 105 into shaped sections 120, 135. The size, shape and filter characteristics of the filters 115, 130 and shaped sections 120, 135 may vary based on a number of factors such as the size, shape and relative position of the one or more vessels to be protected by the device 100 as well as the particle size selected for filtration and the desired amount of blood flow through the filter 100. These and other details of the component parts, various embodiments and uses for embodiments of the filter 100 are described below.

Figure 2:
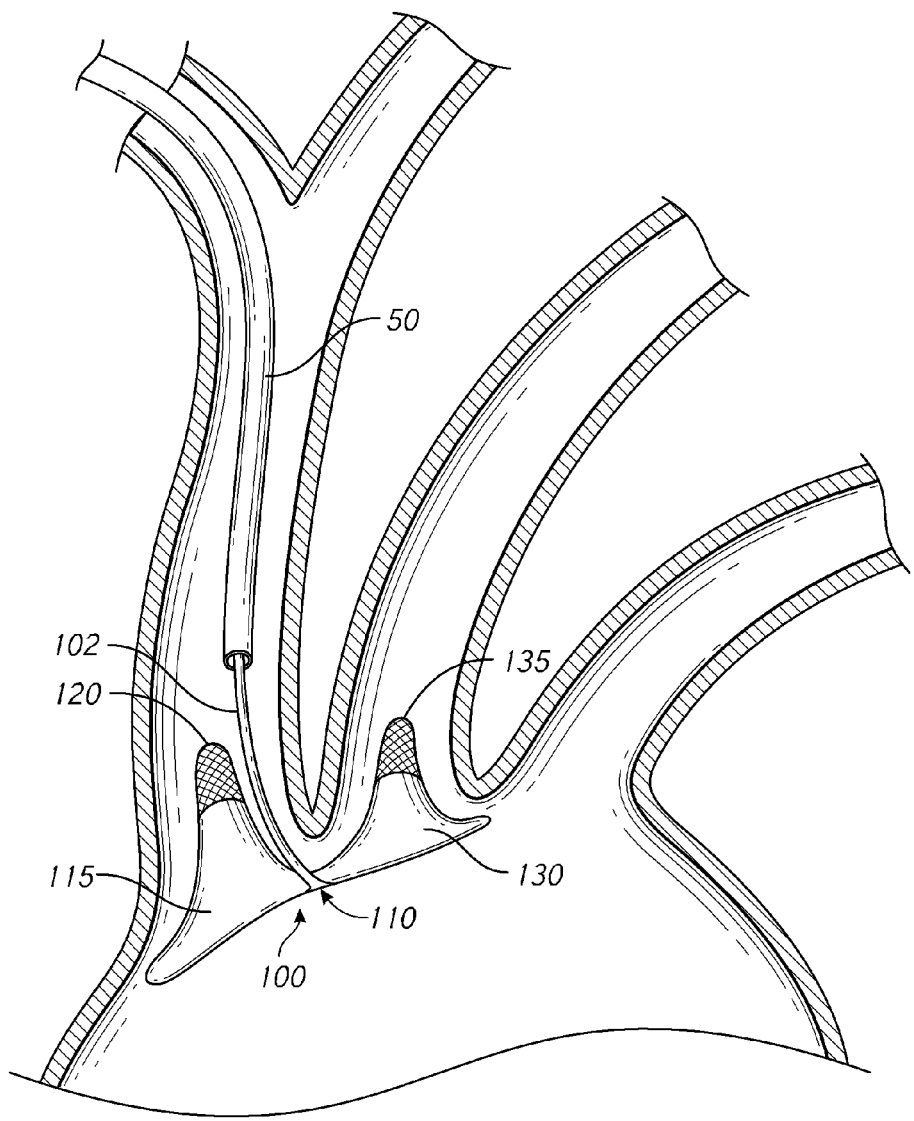
FIG. 2 depicts the filter device delivered and protecting the innominante artery and the left common carotid artery with the self expanding frame and the dome filter material protruding into each vessel.

The device 100 is simple to place and carries only the risk of catheterizing the aorta through the arm or leg, which is minimal. In use as shown in FIG. 2, the device is opened in the thoracic aorta and positioned to cover the ostia of both the innominate and left common carotid arteries and at least a portion of the device will partially enter the innominate and left common arteries. In the illustrated embodiment all or a portion of the shaped sections 120, 135 are within the protected vessel or vessels. This position prevents clots or debris from entering the cerebral circulation through either the right or left carotid arteries with one simple device. Any debris from the cardiac or aortic procedure is captured in the paraboloid of revolution shape 120, 135 protruding into each vessel from the filter 100.

Figure 3:
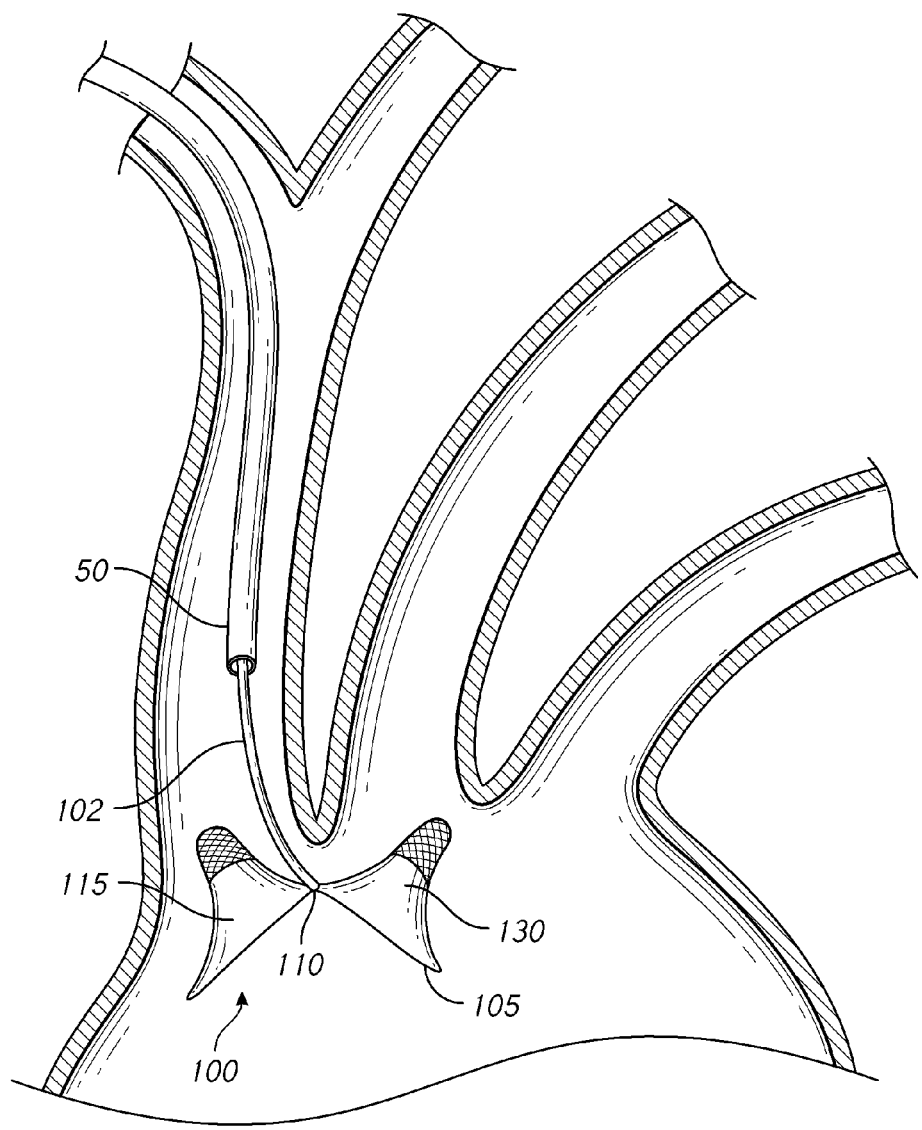
FIG. 3 depicts the device being closed and capturing the embolic material within each dome filter.
Figure 4:
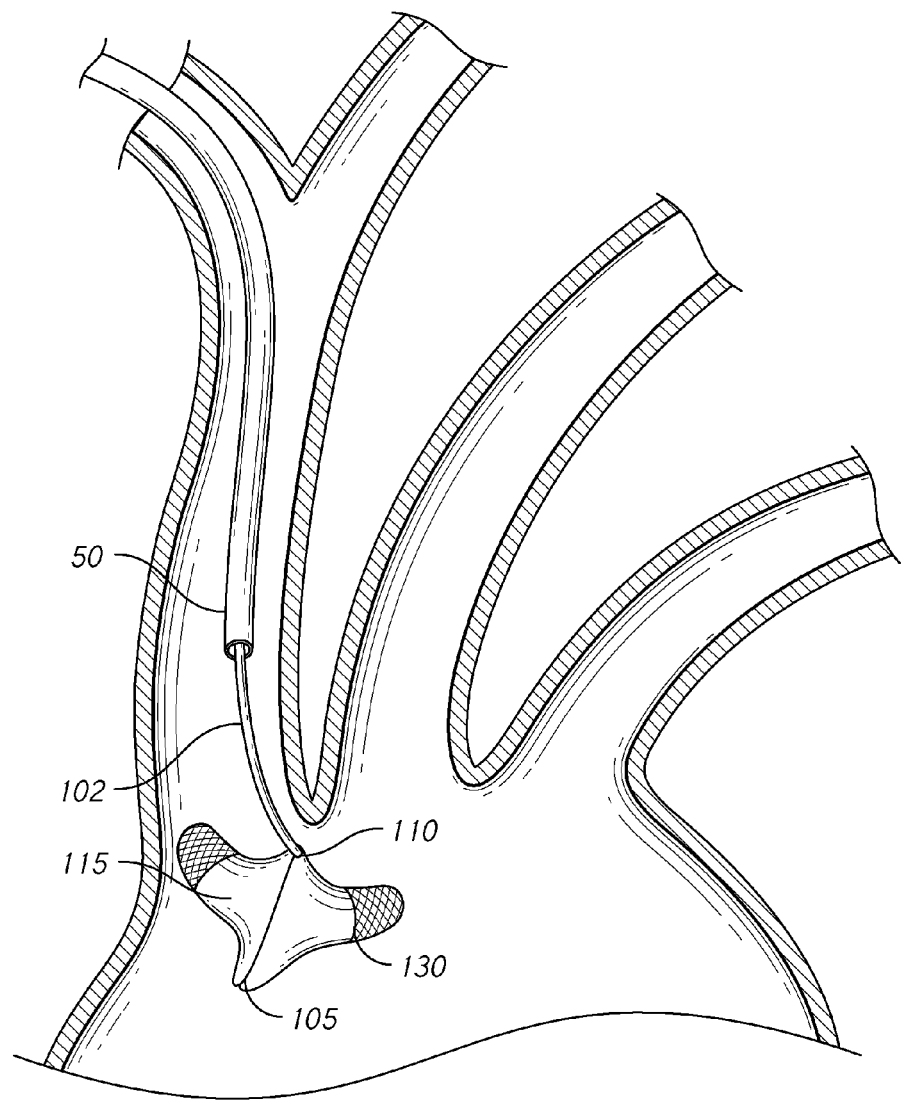
FIG. 4 depicts the domes closed at a common hinge point to trap the embolic material within the filter and ready to be withdrawn from the body.
Figure 5:
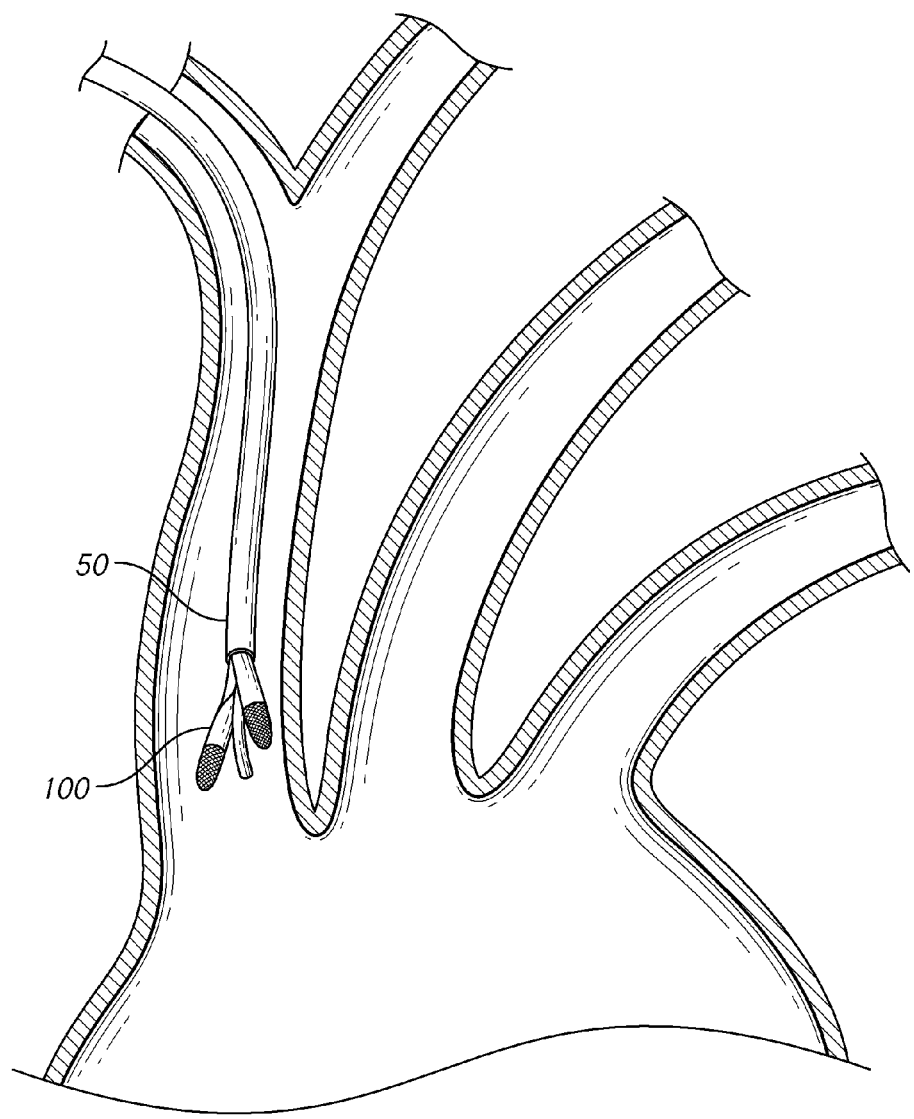
FIG. 5 depicts the filter device being drawn back into the catheter ready to be removed from the body.

After the procedure is complete, the device is inverted by means of a sheath 50 extended over the shaft or connection element 102, which then wholly or partially covers the inverted device prior to withdrawal. As shown in FIGS. 3, 4 and 5, should any clot or debris be captured in the paraboloid of revolution 120, 135, the clot or debris will be captured when inverted via common hinge point 110 and withdrawn along with the device 100. The protrusion or depth of vessel entry of the shaped sections 120, 135 into each of the vessels may vary depending upon a number of factors such as expected particle or emboli size, amount or interaction with the filter 100. In one specific example, the shaped section portion of the filter extends from about 0.5 centimeters to about 3.0 centimeters measured from the device frame 105 positioned in the aorta. The material 115, 130 protruding into the vessel could be any suitable vascular filter material. For example, filters 115, 130 may be formed from, with or contain a polymeric material such as polyurethane with drilled holes for blood flow to the cerebral vasculature. In one aspect, the drilled holes could measure about 100 to 200 microns in diameter but preferably about 130 microns in diameter. Alternatively, the filters 115, 130 may be formed from porous material suited to trapping emboli. The material for filters 115, 130 is selected to allow for adequate filtration where the porous or drilled or formed openings will allow for sufficient blood supply to the cerebral vascular system while stopping any embolic material from traveling throughout the body circulatory system. Trapping and removal of embolic particles within filters 115, 130 rather than merely deflecting material into the aorta is believed to provide a better clinical outcome for the patients. Embolic particles simply deflected back into the aorta will eventually block other blood vessels elsewhere in the body such as the kidneys or lower extremities. As such, embodiments of the device 100 may advantageously be employed to filter out, capture and then remove emboli while also keeping the aorta relatively clear. As best seen in FIG. 2, the frame 110 only remains in the aorta since the filters 115, 130 extend substantially above the plane of frame 105.

The device is preferably concaved-shape with an adequate area to cover the ostia of both the brachiocephalic and left common carotid arteries (FIGS. 1 and 2). The filters 115, 130 may be made of a material with pores (100 to 200 micron) or similar openings or permeability to allow the flow of blood into the cerebral circulation, but able to deflect or trap particles of a size which could cause a stroke. The edge of the frame 105 is preferably a flexible, porous donut shape allowing a good seal with the curved aortic wall. In some embodiments, the edge of the frame 105 will preferably contain a nitinol wire ring or other self-expanding material. The device may have struts or ribs positioned on, in or within frame 105 to assist in the opening and closing of the device and to help maintain its position in use. The device may also be made to open as a result of its construction material, for example, nitinol or polymer, elastically resuming its shape after being released from its sheath.

When the device is to be closed, a tube or sheath 50 is extended over the shaft or connection element 102 until it engages the device. Next, the device is pulled back so that it inverts and is enclosed in the tube for removal (FIGS. 3 and 4). Inverting the device so that the filter openings for each of the filters 115, 130 assures that no trapped particles within filters 115, 130 such as within shaped sections 120, 135 escape into the bloodstream. The components of the device 100 may optionally be constructed of polymer, fabric, metal, or a combination of these or other suitable biocompatible materials. The device may also optionally be equipped with radio-opaque markers or other structural parts which are radio-opaque for aid in placement guidance and/or positioning within the body.

Another embodiment of the device has a rolled edge.

The device may also have a flat porous edge.

Another embodiment of the device has no struts, but instead has a nitinol skeleton.

Another embodiment has multiple wires to position and anchor the device.

Another embodiment of the device has anchors at the edges which help to maintain its position during the procedure.

Another embodiment of the device is parachute-like, with a ring gasket at its edge. The gasket can be a softer material such as, for example without limitation, a silicone polymer or an inflatable membrane such as a balloon member. The profile of an inflatable gasket is generally relatively small and when inflated increases in profile, sealing the contacted portion surrounding the protected vessels. The inflation can be pressurized from the handle portion at the proximal end of the device external to the body with, for example a common endoflator used in interventional cardiology. The gasket would be held firmly in position over the ostia of the brachiocephalic and left common carotid arteries. The billowy porous middle section would deflect or trap clot and debris on its exterior surface while causing minimal resistance in the aorta. The middle portion would be inverted as it is removed by pulling on wires attached to its center, capturing any clot stuck to it.

Alternatively, the center of the device may comprise a screen, which fits more snugly against the aortic wall, with a very small profile, further preventing resistance to downstream aortic bloodflow. Again the device would be removed by inversion, capturing any debris stuck to it prior to removal.

The device may be round, oval or rectangular or of another shape to assist in sealing of the edge against the wall of the aorta, covering the ostia of both the brachiocephalic and left common carotid arteries and maintaining a low profile within the lumen of the aorta.

This device could be modified in size in another embodiment in order to be used to cover the ostia of different vessels.

The device may be coated with materials or pharmalogically active agents that prevent or impair clot formation (e.g., heparin or any other suitable anticoagulant).

The device may be deployed through an artery of the arm, or through the femoral artery. The preferred method would be through the right arm, if possible, as this would allow the device to be pulled back against the aortic wall to place it.

When deployed through the femoral artery, the opening of the device would be different and the device would be pushed against the aortic wall over the brachiocephalic and left common carotid openings rather than being pulled back. A wire would be cannulated into the brachiocephalic artery in this case to ensure correct positioning of the device. The device would be modified to allow this method of delivery and positioning. In one aspect, retrieval of the device would involve inversion and closing of the device by drawstring or another method. For example, pulling, activating, manipulating or otherwise causing movement of the common hinge or frame joint 110.

Brachial Artery Insertion of the Device

The device is delivered via percutaneous insertion into the right brachial artery and is guided into the aortic arch. There it is deployed and then pulled back into position to cover the ostia of the innominate and left common carotid arteries. The device deflects and filters embolic debris during aortic and cardiac procedures, allowing the flow of blood through into the cerebral circulation (carotid arteries) but not permitting the passage of particulate debris.

Femoral Artery Insertion of the Device

The device is delivered via percutaneous insertion into the femoral artery and is guided into the aortic arch. After catheterization of the innominate artery, the device is passed over the wire and brought into position covering the ostia of the innominate and left common carotid arteries.

Deployment of the Device via Arm Approach

Percutaneous access to the circulation via the right arm is performed and a wire guided into the aortic arch after exiting the innominate artery. The device may be placed over the wire or advanced without a guidewire and guided into the aortic arch. The covering outer sheath which encapsulates the device is retracted, exposing the device to the aortic bloodstream. The device is then opened in the aortic arch. The device is pulled back into position, covering the ostia of the innominate and left common carotid artery with a portion of the device entering into each vessel. The device allows the passage of blood through to the carotid arteries, but deflects debris passing along the aorta and filtering any embolic material entering the innominante and left common carotid arteries. At the completion of the debris producing concomitant procedure, the device is closed by inverting the two domes 120, 135. The device is then withdrawn into a covering sheath (FIG. 5) to completely encapsulate it prior to removal from the arm access artery. Any trapped debris is captured in the domes, safely and securely within the catheter.

Embolic Filteration Device

Figure 8:
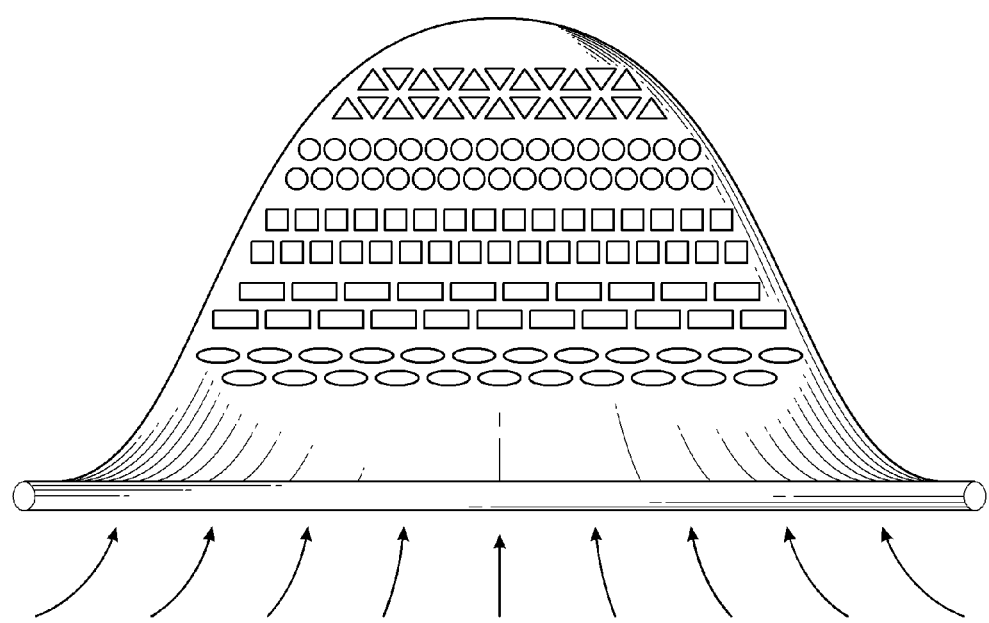
FIG. 8 illustrates a variety of exemplary shapes, sizes, and configurations of holes that can be formed in one or more of the filters.

The device of the present invention, viewed from above, is semi-circular or oval in shape with an adequate diameter of about 15 mm to about 30 mm in the short axis and about 20 mm to about 60 mm in the long axis to cover the ostia of both the brachiocephalic and left common carotid arteries. The filter material may be a polymeric material such as polyurethane or other thin material with a porosity that will allow the flow of blood, but capture particles of a size which could cause a stroke. FIG. 8 illustrates exemplary sizes, shapes, and configuration of the holes that can be formed in a filter. The size and configuration of the holes in the filter could be round in shape but more effectively would be an oval or a slot configuration where the material captured would be smaller but the surface area of the openings could be larger. Other shapes could include triangular or squares to achieve the same function. A square hole would provide about 30 percent more cross sectional area for blood to flow while still capturing the same spherical particle size. The edge of the device is a flexible, porous donut, similar to the edge of a diaphragm, allowing a good seal with the curved aortic wall. The edge will preferably contain a self-expanding material such as Nitinol. The frame of the device may also include struts to assist in the opening and closing of the device and/or to help maintain its position in the relevant anatomy.

The device is constructed of polymer, fabric, metal, or a combination of these materials. The device may be provided with radioopaque markers or metal parts which are radioopaque.

Another embodiment of the device has a rolled edge. The device could also have a flat porous edge. Another embodiment of the device has no struts, but a nitinol skeleton. Another embodiment has multiple wires to position and anchor the device. Another embodiment of the device has anchors at the edges which help to maintain its position during the procedure.

Another embodiment of the device is parachute-like, with a ring gasket at its edge. The gasket would be held firmly in position over the ostia of the brachiocephalic and left common carotid arteries.

Embodiments of the filter 100 may be configured for self locking and/or self sealing with or within the anatomy of the filter site. Self lock or self sealing may be accomplished by releasing a stowed filter from a sheath or other restraint or otherwise activity or actuating the device into a locked or sealing configuration.

Alternatively, the filter may be released into the vasculature and then urged into a locked or sealed configuration. In one aspect, a locking device is positioned outside the body that is adapted and configured to permit movement of or adjusted to the filter relative to the filter site to seal and/or lock the position and configuration of the filter. When the desired position and configuration is achieved the external locking device is used to hold the filter in position and maintain the desired configuration.

Figure 6:
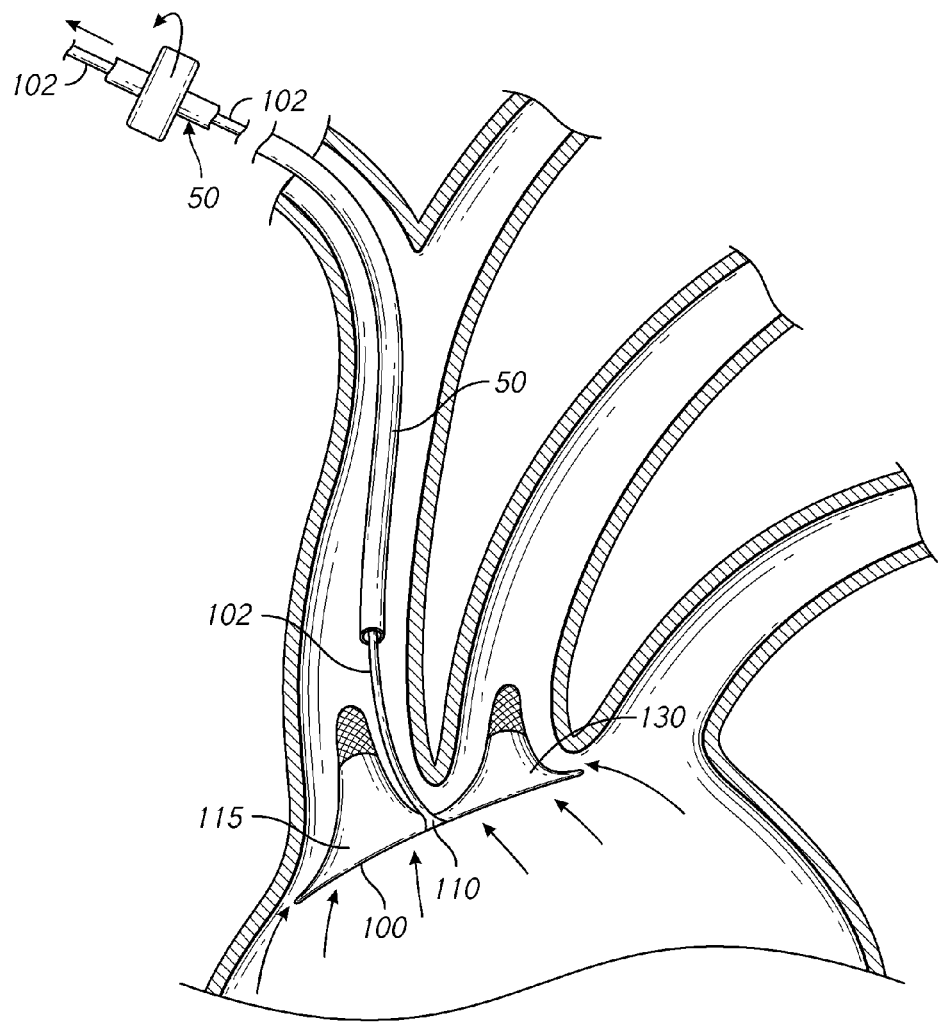
FIG. 6 illustrates a filter positioned within the aorta and connected to a locking device (unlocked configuration).
Figure 7:
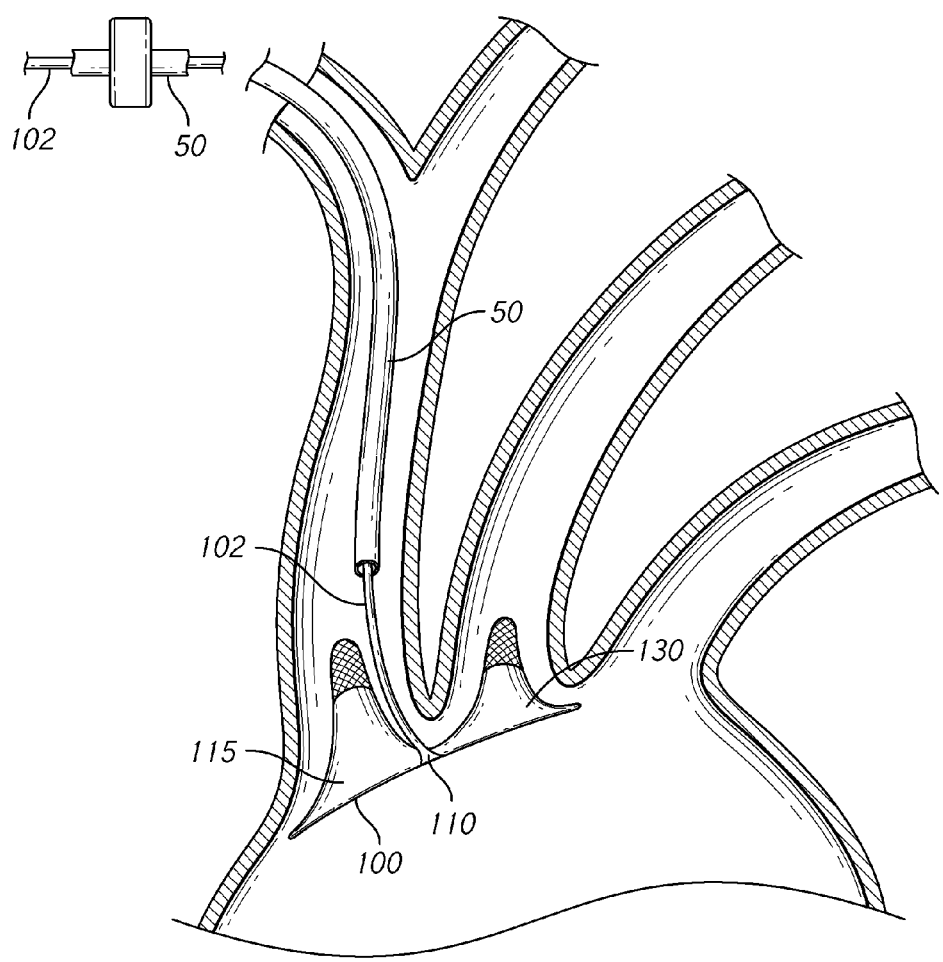
FIG. 7 illustrates the filter of FIG. 6 after tensioning the filter into a sealing arrangement within the aorta and protected vessels and restraining the filter with the locking device (locked configuration).

In one specific aspect, once the desired filter device position is obtained, a locking mechanism relative to the body could hold tension between the device and the aortic wall to maintain a proper blood seal. This could be achieved by tensioning the connection of the device within the body via delivery catheter and a clamp or fixation device between the introducer sheath and tensioned member. A good example of this would be a RHV (rotating hemostaic valve) mounted to the introducer sheath allowing the tensioned connection member to pass through the central lumen. As the tension is added to the central member the RHV could be rotated causing an interference force between the two creating a lock where the tension is now carried by the introducer sheath which is external to the body and the internal filter device which is held in tension along the aortic wall without constant human interaction pulling the device relative to the introducer sheath now needed. Turning now to the example of FIGS. 6 and 7. FIG. 6 illustrates the filter deployed within the aorta but not yet sealed with the anatomy. A locking mechanism, here a rotating hemostasis valve, is used to allow movement between and lock the relative position of the element 102 connected to the filter (i.e. a guidewire) and the sheath 50 used to deliver the filter. After pulling the filter into a sealing arrangement with the appropriate vessels, the RHV may be locked thereby securing the filter relative to the sheath and the entire device relative to the anatomy. The RHV in the illustrative embodiment may be replaced by any suitable locking device that provides the adjustment, sealing and securing characteristics described above.

The billowy porous middle section would deflect or trap clot and debris on its exterior surface while causing minimal resistance in the aorta. The middle portion would be inverted as it is removed by pulling on wires attached to its center, capturing any clot stuck to it. Alternatively, the center of the device could be a screen, which fits more snugly against the aortic wall, with a very small profile, further preventing resistance. Again the device would be removed by inversion, capturing any clot stuck to it prior to removal.

The device may be round, oval or rectangular or of another shape to assist in sealing of the edge against the wall of the aorta, covering the ostia of both the brachiocephalic and left common carotid arteries and maintaining a low profile within the lumen of the aorta. This device could be modified in size in another embodiment in order to be used to cover the ostia of different vessels. The device may be coated with something which prevents clots (e.g. heparin).

Any of the features of the filter devices and methods of use described herein can be incorporated into any of the filter devices and methods of use described in U.S. Patent Publication No. 2010/0179647, U.S. Patent Publication No. 2010/0179585, U.S. Patent Publication No. 2010/0179584, U.S. Patent Publication No. 2010/00179583, and U.S. Patent Publication No. 2008/0065145 (and vice versa), all of which are incorporated by reference herein. For example, the disclosure herein includes embodiments in which the emboli deflection element from the Patent Applications recited above is replaced with first and second emboli trapping filters, examples of which are described herein.

While the invention has been described in its preferred embodiments, it is to be understood that the words which have been used are words of description rather than of limitation and that changes may be made within the purview of the appended claims without departing from the true scope and spirit of the invention in its broader aspects. Rather, various modifications may be made in the details within the scope and range of equivalents of the claims and without departing from the spirit of the invention. The inventor further requires that the scope accorded the claims be in accordance with the broadest possible construction available under the law as it exists on the date of filing hereof (and of the application from which this application obtains priority, if any) and that no narrowing of the scope of the appended claims be allowed due to subsequent changes in the law, as such a narrowing would constitute an ex post facto adjudication, and a taking without due process or just compensation.

What is claimed is:

1. A method of filtering and capturing particles in the vasculature, comprising the steps of:
    providing delivery device with a filter device positioned therein, the filter device comprising a frame and first and second filter portions secured to the frame, wherein the frame has a folded configuration whereby the first and second filter portions are folded by pivoting about an axis positioned between portions of the first and second filter portions closest to each other and a deployed configuration;
    advancing the delivery device through a first vessel;
    deploying the filter device from the delivery device;
    with the delivery device positioned in the first vessel, positioning the first filter portion relative to the first vessel such that particles traveling into the first vessel will be trapped in the first filter portion and that an open portion of the first filter portion faces forward away from the delivery device;
    with the delivery device positioned in the first vessel, positioning the second filter portion relative to a second vessel such that particles traveling into the second vessel will be trapped in the second filter portion and that an open portion of the second filter portion faces forward away from the delivery device; and
    pivoting the first and second filter portions toward one another about the axis to bring the open portions of the first and second filter portions towards each other to capture the particles trapped in the first and second filter portions.

2. The method of claim 1 wherein the deploying step comprises deploying the filter device from within a delivery device to allow the frame to reconfigure from the folded configuration to the deployed configuration.

3. The method of claim 1 wherein after the positioning steps further comprising the step of proximally retracting the frame into a sealing arrangement with the first and second vessels.

4. The method of claim 1 further comprising the step of locking the position of the filter device relative to the first and second vessels.

5. The method of claim 1 wherein the folding step comprises folding the frame about a common joint from the deployed configuration to the folded configuration, wherein folding the frame prevents particles from being released from the first and second filter portions.

6. The method of claim 1 wherein during the deploying step the frame is reconfigured from the folded configuration to the deployed configuration while in the thoracic aorta.

7. The method of filtering and capturing particles according to claim 1 which method comprises protecting the cerebral vasculature from particles dislodged during an endovascular procedure.

8. The method of claim 7 wherein the positioning steps further comprise positioning the first and second filter portions such that at least a portion of one of the first or second filter portions is in the innominate artery and at least a portion of the other filter portion is in the left common carotid artery.

9. The method of claim 8 wherein the frame remains in the thoracic aorta during the endovascular procedure.

* * * * *